United States Patent [19]

Kane et al.

[11] Patent Number: 4,775,688

[45] Date of Patent: Oct. 4, 1988

[54] 5-ARYL-2,4-DIALKYL-3H-1,2,4-TRIAZOLE-3-THIONES AND THEIR USE AS ANTIDEPRESSANTS

[75] Inventors: John M. Kane, Cincinnati; Francis P. Miller, Loveland, both of Ohio

[73] Assignee: Merrell Dow Pharmaceuticals Inc., Cincinnati, Ohio

[21] Appl. No.: 51,103

[22] Filed: May 15, 1987

Related U.S. Application Data

[63] Continuation of Ser. No. 807,613, Dec. 11, 1985, abandoned, which is a continuation-in-part of Ser. No. 792,359, Oct. 29, 1985, abandoned.

[51] Int. Cl.$^4$ .................... A61K 31/41; C07D 249/10
[52] U.S. Cl. ..................................... 514/384; 548/263
[58] Field of Search ............... 514/383, 384; 548/263, 548/265

[56] References Cited

U.S. PATENT DOCUMENTS 3,514,466  5/1970  Stable et al. .................... 548/263

OTHER PUBLICATIONS

Kubota et al., Chem Pharm Bull. 23 (5) 955–966 (1975) 1,2,4-triazoles. IV. Tautomerism of 3,5 di-substituted triazoles.
Sandstrom et al., ACTA Chemica Scandinavica, vol. 20, pp. 57–71, (1966).
Hoggarth, Compounds Related to Thiozinecarbazide, Part I, J. Chem-Soc, pp. 1160–1163 (1949).

*Primary Examiner*—Richard L. Raymond
*Assistant Examiner*—D. L. Dinner
*Attorney, Agent, or Firm*—Edlyn S. Simmons; R. A. McDonald

[57] ABSTRACT

This invention relates to novel 5-aryl-2,4-dialkyl-3H-1,2,4-triazole-3-thiones, to the intermediates and processes for their preparation, and to their use as antidepressants.

20 Claims, No Drawings

5-ARYL-2,4-DIALKYL-3H-1,2,4-TRIAZOLE-3-THIONES AND THEIR USE AS ANTIDEPRESSANTS

This application is a continuation application of our co-pending application Ser. No. 807,613 now abandoned filed Dec. 11, 1985, which in turn is a continuation-in-part application of then-pending application Ser. No. 792,359 now abandonded filed Oct. 29, 1985, now abandoned.

BACKGROUND OF THE INVENTION

This invention relates to 5-aryl-2,4-dialkyl-3H-1,2,4-triazole-3-thiones, to the intermediates and processes for their preparation, to their pharmacological properties, and to their use as antidepressants.

More specifically, this invention relates to compounds of the formula

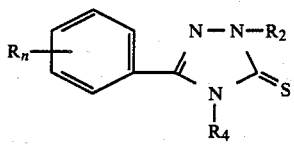

I and the tautomers thereof, wherein R represents halogeno, $C_{1-6}$ lower alkyl, $C_{1-6}$ lower alkoxy, hydroxy, methylenedioxy or trifluoromethyl with n being 1 or 2, and each of $R_2$ and $R_4$ independently represent $C_{1-6}$ lower alkyl.

Preferably halogeno represents chloro or fluoro, and methyl and ethyl represent the preferred lower alkyl moieties, although all the straight, branched and cyclic manifestations thereof such as n-propyl, cyclopentyl, cyclohexyl and cyclopropyl are herein included. Lower alkoxy radicals includes ethers having alkyl moieties paralleling the $C_{1-6}$ alkyl group. Preferably n is one representing a mono-substituted phenyl moiety with the R-substituted being a group located at any of the ortho, meta or para positions, although the para-substituted compounds are preferred. When di-substituted (i.e., n is 2), the 2,3-, 2,4-, 2,5-, 2,6-, 3,4-, or 3,5- positions are contemplated. The tautomeric forms are included for each of the compounds embraced within formula I. Preferably $R_2$ and $R_4$ each represent an alkyl group, especially methyl or ethyl.

The compounds of formula I may readily be prepared using processes and procedures analogously known in the art as seen by the following reaction scheme.

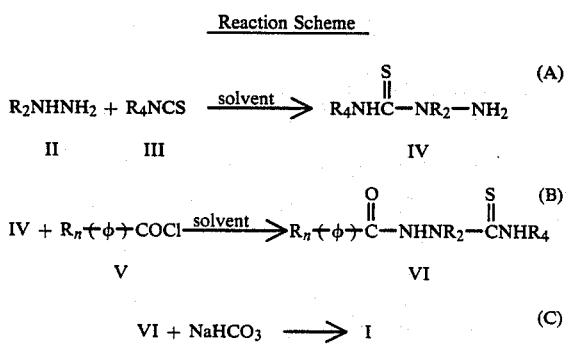

wherein $R_2$, $R_4$, $R_n$ are as defined above and (Φ) represents phenyl.

In step A, the preparation of the thiosemicarbazides (IV) is readily effected by reacting a hydrazine (II) with an isothiocyanate (III) by contacting the reactants in a suitable solvent. The reaction is quite rapid and may be carried out at 0° C. to room temperature. Although the reaction proceeds rapidly, the mixture may be left for up to 24 hours without significant decrease in yields. Reflux conditions may be employed but are not preferred. Almost all solvents (with the exception of water and organic acids) may be used. Anhydrous alcohols (preferably ethanol or methanol) are preferred although DMF, $CHCl_3$, $CH_2Cl_2$, THF and $Et_2O$ may also be used. The required hydrazines and isothiocyanates are readily available but may be prepared by known techniques quite obvious to one of ordinary skill in the art.

In Step B, the desired benzoyl-substituted thiosemicarbazides (VI) may be prepared by reacting the thiosemicarbazides (IV) with an R-substituted-benzoyl chloride (V) in an aprotic solvent such as pyridine, $CHCl_3$, THF and the like. The acylation proceeds rather easily at temperatures ranging from 0° C. to room temperature over periods of 3 to 24 hours although elevated temperatures (e.g. reflux temperatures) may be employed. Again, the acid halides (V) generally are commercially available but may also be prepared from the corresponding acids which are available from obvious starting materials.

In Step C, the benzoyl thiosemicarbazides (VI) are subjected to a cyclization reaction which is effected by heating the compounds (VI) in an aqueous base, preferably using 1 molar equivalent of the base (e.g. sodium bicarbonate or sodium hydroxide). Alcoholic bases may be utilized but generally are less desirable. The reaction is conducted at about the reflux temperature of the solvent, preferably at about 65°–100° C. In practice, the thiosemicarbazides (VI) need not be purified for use in Step C so that even 1:1 mixtures with pyridine hydrochloride may be used.

The following specific examples are given to illustrate the preparation of the compounds of this invention although the scope of compounds exemplified is not meant to be limiting, this being so in view of the ease by which the compounds of formula I may be prepared. Interchange, or modification, and employment of the necessary intermediates and solvents are quite obvious to a chemist of ordinary skill.

Preparation of $R_2,R_4$-Substituted-Thiosemicarbazides

EXAMPLE 1

2,4-DIMETHYLTHIOSEMICARBAZIDE

To a stirred solution of methyl hydrazine (16.0 ml, $3.00 \times 10^{-1}$ mole) and sieve dry ethanol (50 ml) was added dropwise a solution of methyl isothiocyanate (22.0 g, $3.00 \times 10^{-1}$ mole) mole) and sieve dry ethanol (30 ml). The reaction is exothermic and gently refluxes as the isothiocyanate is added. A precipitate soon forms. After stirring overnight, the reaction was cooled in an ice bath. The precipitate was then collected by filtration, washed with a little cold isopropanol, and dried by suction affording a pale yellow powder: 26.7 g (75%). This material was crystallized two times from water and two times from isopropanol affording small colorless needles: 14.7 g (41%), mp=135°–137° C.

Preparation of $R_n$1-Benzoyl-$R_2$, $R_4$-Thiosemicarbazides

EXAMPLE 2

1-(4-Chlorobenzoyl)-2,4-Dimethylthiosemicarbazide

To a stirred solution of 2,4-dimethylthiosemicarbazide (1.19 g, $1.00 \times 10^{-2}$ mole) and pyridine (10 ml) was added dropwise 4-chlorobenzoyl chloride (1,3 ml, $1.02 \times 10^{-2}$ mole). The reaction turns yellow and a mild exotherm is noted. After stirring overnight the reaction was evaporated to dryness affording a beige solid: 3.61 g (97%) which represents a mixture of the desired 1-(4-chlorobenzoyl)-2,4-dimethylthiosemicarbazide and pyridine hydrochloride. In general this mixture was used without further purification in the subsequent cyclization step. If pure 1-(4-chlorobenzoyl)-2,4-dimethylthiosemicarbazide is desired, the above mixture is treated with water and that which does not dissolve is collected by filtration. After drying by suction this material is crystallized from ethanol affording colorless matted needles: 1.03 g (40%), mp=206°–208° C. (decomp).

Preparation of Final Products

EXAMPLE 3

5-(4-Chlorophenyl)-2,4-Dimethyl-3H-1,2,4-Triazole-3-Thione

The 1:1 mixture of 1-(4-chlorobenzoyl)-2,4-dimethylthiosemicarbazide and pyridine hydrochloride (3.61 g of mixture) from Example 2 and 1 molar aqueous NaHCO$_3$ (100 ml, $1.00 \times 10^{-1}$ mole) were stirred and warmed to reflux. After refluxing for 5 hours the reaction was allowed to cool. It was then placed in a refrigerator for several hours before the precipitate was collected by filtration. The collected material was dried partially by suction before being transferred to a desiccator where it was dried at high vacuum. This affords the desired product as a beige powder: 2.01 g (84%). This was purified by flash chromatography and subsequent crystallization from isopropanol yielding small, slightly yellowish plates: 1.74 g (73%), mp 113°–115° C.

In a similar manner by substituting the reactants of examples 1–3 with appropriate $R_2$, $R_4$-substituted reactants, and by substantially following the techniques therein, the following compounds are readily prepared.

FORMULA I

| Ar | $R_2$ | $R_4$ | M.P. |
|---|---|---|---|
| 2-ClC$_6$H$_4$ | CH$_3$ | CH$_3$ | 138–140° |
| 4-ClC$_6$H$_4$ | CH$_3$ | CH$_3$ | 114–116° |
| 4-ClC$_6$H$_4$ | CH$_3$ | C$_2$H$_5$ | 113–115° |
| 4-ClC$_6$H$_4$ | CH$_3$ | n-C$_3$H$_7$ | 240–250°/0.55 mm |
| 4-ClC$_6$H$_4$CH$_2$ | CH$_3$ | CH$_3$ | 142–144° |
| 2,4-Cl$_2$C$_6$H$_3$ | CH$_3$ | CH$_3$ | 135–137° |
| 3,4-Cl$_2$C$_6$H$_3$ | CH$_3$ | CH$_3$ | 161–163° |
| 2,6-Cl$_2$C$_6$H$_3$ | CH$_3$ | CH$_3$ | 115–116° |
| 2-FC$_6$H$_4$ | CH$_3$ | CH$_3$ | 106–108° |
| 3-FC$_6$H$_4$ | CH$_3$ | CH$_3$ | 126–128° |
| 4-FC$_6$H$_4$ | CH$_3$ | CH$_3$ | 130–132° |
| 2,4-F$_2$C$_6$H$_3$ | CH$_3$ | CH$_3$ | 102–104° |
| 2,6-F$_2$C$_6$H$_3$ | CH$_3$ | CH$_3$ | 158–160° |
| 3-CF$_3$C$_6$H$_4$ | CH$_3$ | CH$_3$ | 73–75° |
| 4-CH$_3$C$_6$H$_4$ | CH$_3$ | CH$_3$ | 94–96° |
| 4-CH$_3$OC$_6$H$_4$ | CH$_3$ | CH$_3$ | 96–98° |
| 3,4-OCH$_2$OC$_6$H$_3$ | CH$_3$ | CH$_3$ | 142–144° |
| 4-CH$_3$O—3-(n-C$_4$H$_9$O)C$_6$H$_3$ | CH$_3$ | CH$_3$ | 95–97° |
| 4-CH$_3$O—3-(cyclo-C$_5$H$_9$O)C$_6$H$_3$ | CH$_3$ | CH$_3$ | 175–177° |

Other compounds embraced within formula I may similarly be prepared by using the procedures of Example 1–3.

Using standard laboratory methodology, the pharmacological properties, and their relative potencies, may readily be determined. When compared with other agents clinically known to be useful as antidepressants, the dosage regimen may readily be ascertained by those of ordinary skill in the art.

For example, the assay testing for prevention of reserpine-induced ptosis in mice and in rats is a standard assay. In those test groups, weighed mice or rats are housed individually in wire mesh stick cages and administered test compound or vehicle. At a selected time thereafter, reserpine, prepared as a 4 mg/ml solution in dilute acetic acid, is given to rats at a dose of 4 mg/kg subcutaneously, and to mice as a 0.2 mg/ml solution in dilute acetic acid at a dose of 2 mg/kg intravenously into a tail vein. In each assay the animals are examined individually in a plexiglass cylinder 90 minutes later. Prevention or delay in ptosis is considered significant if the average closure of both eyes is less than 50% after observing for 30 seconds. The ED50 for prevention of ptosis is defined as the dose of test compound that significantly prevents ptosis in 50% of the test animals.

In these tests imipramine has an ED50 of 2.6 mg/kg (using a 30 minute pre-treatment time) in rats whilst 5-(4-chlorophenyl)-2,4-dimethyl-3H-1,2,4-triazole-3-thione has an ED50 of 0.14 under the same conditions. In mice, imipramine, at a 60 minute pre-treatment time, has as ED50 of 4.1 mg/kg whilst 5-(4-chlorophenyl)-2,4-dimethyl-3H-1,2,4-triazole-3-thione has an ED50 of 0.27 under the same conditions. 5-(4-Chlorophenyl)-2,4-dimethyl-3H-1,2,4-triazole-3-thione is one of the more potent compounds compounds of this invention.

Another assay utilized to evaluate antidepressant activity is testing for the antagonism to RO-4-1284* -induced hypothermia. (*Niemegeers, Carlos, J.E. "Antagonism of Reserpine - Like Activity", edited by S. Fielding and Lal, published by Futura, pg. 73–98.) In this test, groups of male mice are weighed and housed individually in wire mesh stick cages. The rectal temperature of each mouse is recorded and the test compound or vehicle is then administered. At a selected time thereafter, RO-4-1284, prepared as a 2 mg/ml solution in distilled water, is administered at a dose of 20 mg/kg i.p. Mice are then placed in a cold room (36° F.) for 30 minutes, and then returned to room temperature for 30 minutes. At this time (60 minutes after RO-4-1284 administration) the rectal temperature of each mouse is again recorded. Under these conditions, RO-4-1284 causes a fall in rectal temperature of 10° to 12° C. The final temperatures of control groups of ten RO-4-1284-treated mice from a number of experiments are combined to form an "historic control" of 100 mice. This control is updated periodically by replacement of the oldest data. Any drug-treated animal which has a final temperature (after RO-4-1284) which is greater than the mean +2 S.D. of the RO-4-1284 historic control is considered to exhibit significant antagonism to the hypothermic effect of RO-4-1284. The ED50 for antagonism is defined as that dose of test compound which significantly antagonizes RO-4-1284 hypothermia in 50% of the test animals.

Using a 60 minute pre-treatment time and these criteria for evaluation of effects, desipramine was found to have an ED50 of 0.1 mg/kg i.p.; imipramine, an ED50 of 1.8 mg/kg i.p., Catron ®, an ED50 of 0.7 mg/kg i.p., and 5-(4-chlorophenyl)-2,4-dimethyl-3H-1,2,4-triazole-0.34 mg/kg i.p.

It is expected that based upon standard laboratory methodology, as well as comparative studies with known agents, the compounds of this invention have pharmacological effects generally attributed to anti-depressants and thus the compounds of this invention will elevate mood in patients suffering from depression and therefore will have an end-use application of treating patients suffering from endogenous depression, a term used interchangeably with psychotic or involutional depression. In this use, the compound (I) will exert a relatively quick onset of action and have a prolonged duration of activity. In general, the compounds are expected to exert their anti-depressant effects at dose levels of about 0.25–25 mg/kg of body weight per day although, of course, the degree of severity of the disease state, age of the patient and such other factors determined by the attending diagnostician will influence the exact course and dosage regimen suitable for each patient. In general the parenterally administered doses are about ¼ to ½ that of the orally administered dose.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose or cornstarch. In another embodiment the compounds of general formula I can be tableted with conventional tablet bases such as lactose, sucrose and cornstarch; in combination with binders, such as acacia, cornstarch or gelatin; disintegrating agents such as potato starch or alginic acid; and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water, alcohols, oils and other acceptable organic solvents with or without the addition of a surfactant and other pharmaceutically acceptable adjuvants. Illustrative of oils which can be employed in these preparations are those of petroleum, animal, vegetable, or synthetic origin; for example, peanut oil, soybean oil and mineral oil. In general, water, saline, aqueous dextrose, and related sugar solutions, ethanol, and glycols such as propylene glycol or polyethylene glycol or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic ®, a silicone rubber manufactured by the Dow-Corning Corporation.

As is true in many classes of compounds generally suitable for any particular pharmacological activity having a therapeutic end-use application, certain subgeneric groups and certain specific members of the class, because of their overall therapeutic index, biochemical and pharmacological profile, are preferred. In this instance the preferred compounds are those wherein both $R_2$ and $R_4$ groups are methyl or ethyl, those wherein the R substituent is chloro or fluoro, those wherein the $R_n$ substituent is a monochloro or monofluoro substituent preferably located at the 4-position, and those wherein $R_n$ is a dichloro or difluoro substituent preferably at the 2,4- or 2,6 position. Specifically preferred compounds are:

5-(4-chlorophenyl)-2,4-dimethyl-3H-1,2,4-triazole-3-thione 5-(4-fluorophenyl)-2,4-dimethyl-3H-1,2,4-triazole-3-thione 5-(2-fluorophenyl)-2,4-dimethyl-3H-1,2,4-triazole-3-thione 5-(2,6-difluorophenyl)-2,4-dimethyl-3H-1,2,4-triazole-3-thione 5-(3-fluorophenyl)-2,4-dimethyl-3H-1,2,4-triazole-3-thione 5-(4-methylphenyl)-2,4-dimethyl-3H-1,2,4-triazole-3-thione 5-(2,4-dichlorophenyl)-2,4-dimethyl-3H-1,2,4-triazole-3-thione 5-(2,4-difluorophenyl)-2,4-dimethyl-3H-1,2,4-triazole-3-thione 5-(3,4-difluorophenyl)-2,4-dimethyl-3H-1,2,4-triazole-3-thione In addition to the characteristics discovered for the above described novel compounds of formula I, it has been found that the prior art compound—2,4-dimethyl-5-phenyl-3H-1,2,4-triazole-3-thione—also exhibits pharmacological properties similar to those possessed by the compounds of formula I and thus this compound is also useful as an antidepressant. The compound may be pharmaceutically formulated and administered in a manner similar to that described above for the novel compounds of formula I.

We claim:

1. A method for treating a patient suffering from mental depression which comprises administering an anti-depressant amount of a compound of the formula

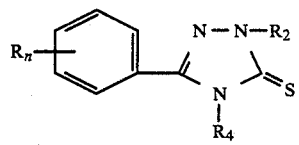

and the tautomers thereof, wherein

R is hydrogen, halogeno, $C_{1-6}$ lower alkyl, $C_{1-6}$ alkoxy, hydroxy, trifluoromethyl, or methylenedioxy, n is 1 or 2, $R_2$ and $R_4$ independently represent $C_{1-6}$ lower alkyl.

2. A method of claim 1 wherein R is halogeno.

3. A method of claim 2 wherein n is one.

4. A method of claim 2 wherein n is two.

5. A method of claim 1 wherein $R_2$ and $R_4$ each are methyl.

6. A method of claim 5 wherein R is $C_{1-6}$ alkyl and n is one.

7. A method of claim 5 wherein R is fluoro and n is one.

8. A method of claim 5 wherein R is fluoro and n is two.

9. A method of claim 5 wherein R is chloro and n is one.

10. A method of claim 5 wherein R is chloro and n is two.

11. A method of claim 9, said compound being 5-(4-chlorophenyl)-2,4-dimethyl-3H-1,2,4-triazole-3-thione.

12. A method of claim 7, said compound being 5-(4-fluorophenyl)-2,4-dimethyl-3H-1,2,4-triazole-3-thione.

13. A method of claim 7, said compound being 5-(2-fluorophenyl)-2,4-dimethyl-3H-1,2,4-triazole-3-thione.

14. A method of claim 8, said compound being 5-(2,6-difluorophenyl)-2,4-dimethyl-3H-1,2,4-triazole-3-thione.

15. A method of claim 7, said compound being 5-(3-fluorophenyl)-2,4-dimethyl-3H-1,2,4-triazole-3-thione.

16. A method of claim 10, said compound being 5-(2,4-dichlorophenyl)-2,4-dimethyl-3H-1,2,4-triazole-3-thione.

17. A method of claim 8, said compound being 5-(2,4-difluorophenyl)-2,4-dimethyl-3H-1,2,4-triazole-3-thione.

18. A method of claim 8, said compound being 5-(3,4-difluorophenyl)-2,4-dimethyl-3H-1,2,4-triazole-3-thione.

19. A method of claim 1, said compound being 5-(4-methylphenyl)-2,4-dimethyl-3H-1,2,4-triazole-3-thione.

20. A method of claim 1, said compound being 2,4-dimethyl-5-phenyl-3H-1,2,4-triazole-3-thione.

* * * * *